United States Patent
Momose et al.

(10) Patent No.: US 10,481,146 B2
(45) Date of Patent: Nov. 19, 2019

(54) GAS SENSOR AND INFORMATION PROCESSING SYSTEM

(71) Applicant: FUJITSU LIMITED, Kawasaki-shi, Kanagawa (JP)

(72) Inventors: Satoru Momose, Atsugi (JP); Kazuaki Karasawa, Hadano (JP); Osamu Tsuboi, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 41 days.

(21) Appl. No.: 15/070,325

(22) Filed: Mar. 15, 2016

(65) Prior Publication Data
US 2016/0341717 A1    Nov. 24, 2016

(30) Foreign Application Priority Data
May 22, 2015  (JP) .................. 2015-104222

(51) Int. Cl.
| | | |
|---|---|---|
| *G01N 27/00* | (2006.01) | |
| *G01N 33/497* | (2006.01) | |
| *G01N 27/12* | (2006.01) | |
| *A61B 5/08* | (2006.01) | |

(52) U.S. Cl.
CPC .......... *G01N 33/497* (2013.01); *G01N 27/12* (2013.01); *A61B 5/082* (2013.01)

(58) Field of Classification Search
CPC ... G01N 27/4077; G01N 33/497; G01N 27/04
USPC .......... 422/82.02, 82.01, 90, 83, 88
See application file for complete search history.

(56) References Cited

U.S. PATENT DOCUMENTS

| | | |
|---|---|---|
| 5,128,020 A | 7/1992 | Yamauchi et al. |
| 2007/0187699 A1 | 8/2007 | Sakata et al. |
| 2010/0112546 A1* | 5/2010 | Lieber ............... A61B 5/14546 435/5 |
| 2011/0089051 A1* | 4/2011 | Wang ............... B82Y 15/00 205/781 |
| 2011/0124113 A1 | 5/2011 | Azad et al. |
| 2013/0115705 A1 | 5/2013 | Patolsky et al. |

FOREIGN PATENT DOCUMENTS

| | | |
|---|---|---|
| CN | 101196489 | 6/2008 |
| DE | 3644819 | 9/1988 |
| EP | 0413419 A1 | 2/1991 |
| GB | 1474246 | 5/1977 |
| JP | 61-200456 | 9/1986 |
| JP | 63-238545 | 10/1988 |
| JP | 2-114168 | 4/1990 |
| JP | 6-82410 | 3/1994 |
| JP | 7-140100 | 6/1995 |
| JP | 2001-289809 | 10/2001 |

(Continued)

OTHER PUBLICATIONS

Non-Final Rejection dated Dec. 11, 2018 for U.S. Appl. No. 15/353,006.

(Continued)

*Primary Examiner* — Natalia Levkovich
(74) *Attorney, Agent, or Firm* — Fujitsu Patent Center

(57) ABSTRACT

A gas sensor includes a p-type semiconductor layer in which a surface at a contacting side with detection target gas is covered with tertiary amine and two electrodes electrically coupled with each other through the p-type semiconductor layer.

5 Claims, 13 Drawing Sheets

(56) References Cited

FOREIGN PATENT DOCUMENTS

| | | |
|---|---|---|
| JP | 2002-031619 | 1/2002 |
| JP | 2003-315299 | 11/2003 |
| JP | 2004-77458 | 3/2004 |
| JP | 2005-221428 | 8/2005 |
| JP | 2007-248335 | 9/2007 |
| JP | 2008-145128 | 6/2008 |
| JP | 2009-19934 | 1/2009 |
| JP | 2009-198346 | 9/2009 |
| JP | 2013-529308 | 7/2013 |
| WO | 0039880 | 7/2000 |

OTHER PUBLICATIONS

ISR—International Search Report dated Sep. 2, 2014 for International Application No. PCT/JP2014/065203.

Written Opinion of the International Searching Authority for International Application No. PCT/JP2014/065203 dated Sep. 2, 2014, with relevant English translation.

Pascal Lauque, et al., "Highly sensitive and selective room tempereture NH3 gas microsensor using an ionic conductor (CuBr) film", Analytica Chimica Acta, 515 (2004), p. 279-284, Elsevier.

P.Lauque, et al., "Electrical properties and sensor characteristics for NH3 gas of sputtered CuBr films", Sensors and Actuators B 59 (1999). p. 216-219, Elsevier.

Marc Bendahan, et al., "Development of an ammonia gas sensor", Sensors and Actuators B 95 (2003), p. 170-176, Elsevier.

P.Lauque, et al., "Electrical Properties of Thin-films of the Mixed Ionic-electronic Conductor CuBr. Influence of Electrode Metals and Gaseous Ammonia", Journal of the European Ceramic Society,1999 vol.19, p. 823-826, Elsevier.

Benjamin Wolpert, et al., "Chemosensitive properties of electrically conductive Cu(I) compounds at room temperature", Sensors and Actuators B 134, 2008, p. 839-842, Elsevier.

ISR—International Search Report dated Sep. 2, 2014 for International Application No. PCT/JP2014/065213.

USPTO—Non-Final Rejection dated Jun. 23, 2017 for U.S. Appl. No. 15/353,028. [issued].

USPTO—Notice of Allowance dated Jan. 16, 2018 for U.S. Appl. No. 15/353,028. [issued].

J.-L. Seguin et al.,"Preparation of thin films of copper(I) bromide by r.f. sputtering: morphology and electrical properties", Thin Solid Films, vol. 323, pp. 31-36, Dec. 31, 1998, Elsevier Science S.A.

CNOA—Office Action of Chinese Patent Application No. 201480079329.X, dated May 30, 2018, with English translation.

JPOA—Office Action of Japanese Patent Application No. 2015-104222, dated Oct. 23, 2018, with relevant machine translation.

CNOA—Chinese Office Action dated Dec. 17, 2018 for Chinese Patent Application No. 201480079329.X, with English translation.

USPTO - Final Rejection dated on May 7, 2019 for U.S. Appl. No. 15/353,006.

\* cited by examiner

FIG. 8

| Gas kind | Selection ratio |
|---|---|
| Ammonia | 0.1 |
| Nonanal | 1 |
| Acetaldehyde | 0.52 |
| Acetone | 0.0024 |
| Ethanol | 0.0042 |

FIG. 11

|  | Selection ratio |
|---|---|
| Ammonia | 1 |
| Acetaldehyde | 0.0034 |
| Ethanol | 0.000213 |

GAS SENSOR AND INFORMATION PROCESSING SYSTEM

CROSS-REFERENCE TO RELATED APPLICATION

This application is based upon and claims the benefit of priority of the prior Japanese Patent Application No. 2015-104222, filed on May 22, 2015, the entire contents of which are incorporated herein by reference.

FIELD

The embodiments discussed herein are related a gas sensor and an information processing system.

BACKGROUND

Conventionally, it is known that useful information relating to a health condition of a person is obtained from odor of the breath or urine of the person.

Research and development for detecting the breath of a person using a gas sensor and finding a disease at an initial stage at which the person does not have a subjective symptom are being proceeded.

For example, a method is examined in which presence or absence of a disease or affection is decided by taking focusing on a specific chemical material in the breath and detecting the specific chemical material using a gas sensor. Especially, if a gas sensor capable of detecting aldehyde with a high sensitivity and besides capable of distinguishing aldehyde from the other substances with a high selection ratio can be implemented, then the gas sensor can be used, for example, for checking of lung cancer or the like.

It is to be noted that, as a sensor for monitoring the concentration of a volatile organic compound in a room, a gas sensor has been proposed which uses a conductive organic-inorganic hybrid material in which organic macromolecules containing, as a main component, poly-naphthylamine, poly amino anthracene or a derivative of the substances are inserted between layers of an inorganic compound containing molybdenum oxide as a main component and which is capable of detecting acetaldehyde preferentially to formaldehyde. Further, as a gas sensor for detecting the freshness of vegetables or the like, also a gas sensor has been proposed which uses a metal oxide such as tin oxide and is capable of detecting aldehydes.

SUMMARY

According to an aspect of the embodiment, a gas sensor includes a p-type semiconductor layer in which a surface at a contacting side with detection target gas is covered with tertiary amine, and two electrodes electrically coupled with each other through the p-type semiconductor layer.

According to an aspect of the embodiment, an information processing system includes the gas sensor described above and a computer configured to process data obtained by the gas sensor.

The object and advantages of the invention will be realized and attained by means of the elements and combinations particularly pointed out in the claims. It is to be understood that both the foregoing general description and the following detailed description are exemplary and explanatory and are not restrictive of the invention.

BRIEF DESCRIPTION OF DRAWINGS

FIG. 8 is a view depicting a result when a response of the gas sensor device of the example to ammonia, nonanal, acetaldehyde, acetone and ethanol is standardized with the concentrations of the gas types using the response to nonanal as a reference to calculate a ratio (selection ratio) to the response to nonanal;

FIG. 11 is a view depicting a result when a response of the gas sensor device of the comparative example to ammonia, acetaldehyde and ethanol is standardized with the concentrations of the gas types using the response to ammonia as a reference to calculate a ratio (selection ratio) to the response to ammonia.

DESCRIPTION OF EMBODIMENTS

A gas sensor has not been implemented successfully which can detect aldehydes with a high sensitivity and can distinguish the aldehydes from the other substances with a high selection ratio to such a degree that the gas sensor can be used, for example, for checking of lung cancer or the like.

Therefore, it is desirable to implement a gas sensor that can detect aldehydes with a high sensitivity and can distinguish the aldehydes from the other substances with a high selection ratio to such a degree that the gas sensor can be used, for example, for checking of lung cancer or the like and an information processing system in which the gas sensor is used.

In the following, a gas sensor and an information processing system according to an embodiment are described with reference to FIGS. 1 to 13.

The gas sensor according to the present embodiment is a gas sensor for detecting chemical substances in the atmosphere, especially a gas sensor for detecting aldehyde (for example, acetaldehyde, nonanal or the like; aldehydes) that is contained in the breath of a person and is a chemical substance that reflects a health condition of the person, and can operate at a room temperature and can be used for checking, for example, of lung cancer. It is to be noted that the gas sensor is hereinafter referred to sometimes as aldehyde gas sensor.

Figure 1:
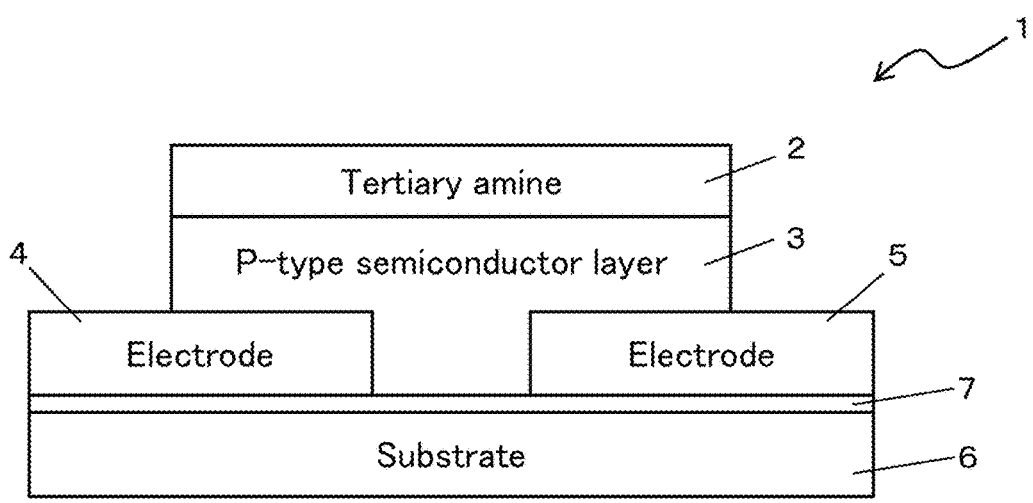
FIG. 1 is a schematic sectional view depicting a configuration of a gas sensor device provided in a gas sensor according to the present embodiment.

As depicted in FIG. 1, the gas sensor of the present embodiment includes a gas sensor device 1. The gas sensor device 1 includes a p-type semiconductor layer 3 whose surface at the side contacting with detection target gas is covered with tertiary amine (tertiary amine layer) 2, and two electrodes 4 and 5 electrically coupled with each other through the p-type semiconductor layer 3. Here, the detection target gas is the breath of a person and is gas that contains aldehyde. It is to be noted that the detection target gas is hereinafter referred to sometimes as measurement target gas.

Here, the p-type semiconductor layer 3 whose surface is covered with the tertiary amine 2 is preferably formed as a layer that interacts intensively with an amino group in an amine molecule. Here, in a compound that contains copper or silver, an ion of the copper or silver forms an intensive coordinate bond with the amino group. Therefore, the p-type semiconductor layer 3 is preferably configured from a p-type semiconductor material that is a compound that contains copper or silver. In other words, the p-type semiconductor layer 3 is preferably configured as a layer that contains copper or silver.

In particular, the p-type semiconductor layer 3 is preferably configured from a p-type semiconductor material containing any one material selected from the group consisting of copper bromide (I) (CuBr), copper oxide (I) ($Cu_2O$), copper sulfide (I) ($Cu_2S$), silver oxide ($Ag_2O$), silver bromide (AgBr) and silver sulfide ($Ag_2S$) that are compounds containing copper or silver. In particular, the p-type semiconductor layer 3 is preferably configured so as to contain any one material selected from the group consisting of cuprous bromide, cuprous oxide, cuprous sulfide, silver oxide, silver bromide and silver sulfide.

Further, the tertiary amine 2 is preferably configured such that all of atom groups bonding to nitrogen atoms of an amino group are an alkyl group. In particular, in order to detect aldehyde capable of being used, for example, as a marker of lung cancer, for example, aldehyde in which hydrogen atoms and an alkyl group are bonding to carbon atoms of a carbonyl group, the tertiary amine 2 is preferably configured such that all of atom groups bonding to nitrogen atoms of an amino group are an alkyl group. Consequently, an intensive response to aldehyde, for example, an aldehyde capable of being used, for example, as a marker of lung cancer can be obtained.

Here, as the tertiary amine 2, for example, N, N-dimethylhexadecylamine or the like may be used.

Further, the two electrodes 4 and 5 are provided in a spaced relationship from each other at the opposite side to the side of the p-type semiconductor layer 3 covered with the tertiary amine 2. Further, the surface of the tertiary amine 2 is exposed so that the detection target gas contacts with at least the surface of the tertiary amine 2 over a region (gap) between the two electrodes 4 and 5.

Here, the two electrodes 4 and 5 (a pair of electrodes) are provided in a predetermined spaced relationship (gap) from each other over a substrate 6 (here, on an insulating film 7 provided on the surface of the substrate 6). Further, the p-type semiconductor layer 3 is provided such that the electrodes are conducted to each other, and the surface of the p-type semiconductor layer 3 at the side contacting with the detection target gas is covered with the tertiary amine 2. Further, the surface of the tertiary amine 2 is exposed such that the detection target gas contacts with the surface of the tertiary amine 2 including the portion over the gap between the two electrodes 4 and 5.

It is to be noted that the gas sensor may be configured such that the p-type semiconductor layer 3 is provided over the substrate 6 and the two electrodes 4 and 5 (a pair of electrodes) are provided in a predetermined spaced relationship (gap) from each other over the p-type semiconductor layer 3 and besides the p-type semiconductor layer 3 whose surface is covered with the tertiary amine 2 contacts with the detection target gas through the gap.

By configuring the gas sensor in such a manner as described above, if aldehyde molecules are absorbed to the p-type semiconductor layer 3 whose surface is covered with the tertiary amine 2, then the electric resistance of the p-type semiconductor layer 3 varies. Therefore, by detecting the variation of the electric resistance of the p-type semiconductor layer 3 whose surface is covered with the tertiary amine 2, aldehyde can be detected. In this manner, the gas sensor of the present embodiment is a gas sensor that detects aldehyde on the basis of the variation of the electric resistance (electric characteristic) arising from absorption of aldehyde molecules.

Further, the gas sensor may be configured such that it includes a detection unit coupled with the two electrodes 4 and 5 and configured to detect the variation of an electric characteristic (here, electric resistance) of the p-type semiconductor layer 3 whose surface is covered with the tertiary amine 2.

For example, the two electrodes 4 and 5 of the gas sensor device 1 may be coupled with a circuit as the detection unit (for example, a circuit including a transistor) through wirings or interconnections and the variation of an electric characteristic (here, electric resistance) of the p-type semiconductor layer 3 whose surface is covered with the tertiary amine 2 is detected by the circuit. It is to be noted that the circuit as the detection unit may be coupled with the two electrodes 4 and 5 through wirings or interconnections and, for example, the circuit and the interconnections may be provided in the insulating film 7 provided on the surface of the substrate 6 or the circuit may be provided on a different substrate coupled thereto through wirings.

By using the p-type semiconductor layer 3 whose surface is covered with the tertiary amine 2 for the detective layer (detection layer) of the gas sensor device 1 provided in the gas sensor as described above, aldehyde can be detected distinctly from the other substances with a high sensitivity and a high selection ratio to such a degree that the gas sensor can be used for checking, for example, of lung cancer or the like.

Here, for example, as regards lung cancer, aldehyde whose carbon number is 5 to 10 can be used as an indicator substance. Especially, nonanal whose carbon number is 9 is suitable as a marker substance and is considered that it can be used for decision of presence or absence of affection using a concentration of approximately 200 ppb at a volume ratio as a threshold value.

By using the p-type semiconductor layer 3 whose surface is covered with the tertiary amine 2 for the detective layer of the gas sensor device 1 provided in the gas sensor as described above, for example, it is possible to detect acetaldehyde having a concentration of approximately 300 ppb or nonanal having a concentration of approximately 200 ppb. In particular, aldehyde such as acetaldehyde or nonanal can be detected with a high sensitivity in a level in which it can be applied to checking of lung cancer.

On the other hand, where the p-type semiconductor layer 3 whose surface is covered with the tertiary amine 2 is used for the detective layer of the gas sensor device 1 provided in the gas sensor, a clear response to ammonia is not found and a response to ketone (for example, acetone) or alcohol (for example, ethanol) is weak. In other words, a difference of the responsibility between aldehyde and ammonia, ketone and alcohol can be increased. In this manner, the present gas sensor has such a high gas type selectivity that the sensitivity to a chemical substance other than aldehyde, namely, to organic gas (gaseous organic compound) such as, for example, ammonia, ketone (for example, acetone) or alcohol (for example, ethanol) is low.

By using the p-type semiconductor layer 3 whose surface is covered with the tertiary amine 2 for the detective layer of the gas sensor device 1 provided in the gas sensor as described above, aldehyde can be detected distinctly from the other substances with a high sensitivity and a high selection ratio to such a degree that the gas sensor can be used for checking, for example, of lung cancer or the like. In particular, the gas sensor can be implemented that has a high sensitivity and exhibits an intensive response to aldehyde in gaseous organic compound. Then, by using such a gas sensor as described above, a simple and convenient lung cancer detection device can be configured and simple examination (diagnosis) of lung cancer using the breath can be implemented.

On the other hand, in the gas sensor that is described in the paragraph of the prior art and for which an organic-inorganic hybrid material wherein organic macromolecules containing, as a main component, poly-naphthylamine or the like are inserted between layers of an inorganic compound that contains molybdenum oxide as a main component is used, a resistance variation rate only of approximately 5% to acetaldehyde having the concentration of 400 ppb is exhibited and the sensitivity is insufficient for the use for checking of lung cancer or the like.

Further, it is preferable for the detective layer of the gas sensor device 1 provided in the gas sensor that the variation of an electric characteristic (here, electric resistance) is great and that the detective layer returns to an original state after gas is detected and besides the recovery speed is high (recovery time period is short). From the points just described, it is preferable to use the p-type semiconductor layer 3 whose surface is covered with the tertiary amine 2 for the detective layer. For example, by using the tertiary amine 2 to cover the surface of the p-type semiconductor layer 3 that configures the detective layer, the variation of an electric characteristic (here, electric resistance) when gas is detected is increased in comparison with an alternative case where primary amine or secondary amine is used. Further, the detective layer can return to an original state after gas is detected and the recovery speed can be increased.

An operation principle where cuprous bromide (CuBr) is used as a material of the p-type semiconductor layer 3 in the gas sensor configured in such a manner as described above is described below.

Figure 2:
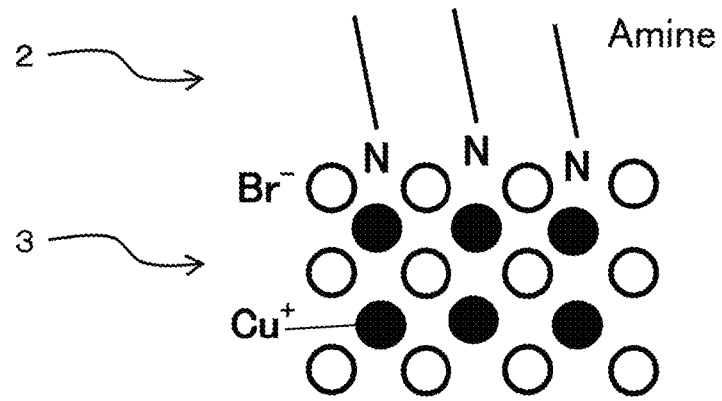
FIG. 2 is a schematic view depicting a region in the proximity of the surface at the side contacting with detection target gas where a detective layer of the gas sensor device provided in the gas sensor according to the present embodiment is configured as a CuBr layer whose surface is covered with tertiary amine.
Figure 3:
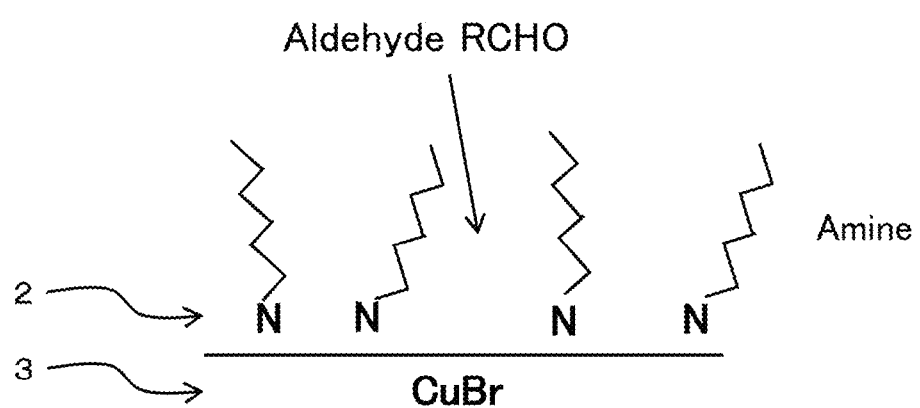
FIG. 3 is a schematic view depicting a manner in which aldehyde molecules come near to the surface of the detective layer where the detective layer of the gas sensor device provided in the gas sensor according to the present embodiment is configured as a CuBr layer whose surface is covered with tertiary amine.

First, nitrogen atoms of an amino group contained in the tertiary amine 2 can form a coordinate bond with a copper ion. Therefore, as depicted in FIG. 2, in a region in the proximity of the surface of the side the p-type semiconductor layer 3 contacting with the detection target gas, the tertiary amine 2 is intensively absorbed in a state in which the amino group is directed to the surface of the CuBr layer as the p-type semiconductor layer 3.

Figure 4:
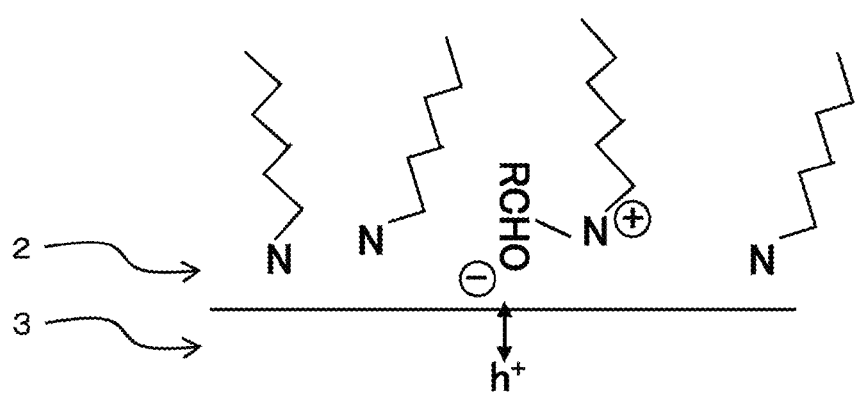
FIG. 4 is a schematic view depicting a manner in which aldehyde molecules absorbed to the surface of the detective layer temporarily form a polarized structure by interacting with an amino group of amine existing on the surface of the detective layer where the detective layer of the gas sensor device provided in the gas sensor according to the present embodiment is configured as a CuBr layer whose surface is covered with tertiary amine.

If aldehyde molecules approach and absorb to such a surface at the contacting side with the detection target gas as described above as depicted in FIG. 3, namely, if an amino group contained in the tertiary amine 2 and aldehyde approach each other, then, as depicted in FIG. 4, nitrogen atoms of the amino group of the tertiary amine 2 perform nucleophilic attack to a carbonyl group of the aldehyde thereby to temporarily form a polarized structure.

If such a polarized structure as just described exists closely to the surface of the CuBr layer as the p-type semiconductor layer 3, then carriers are trapped by the local charge in the proximity of the surface of the CuBr layer 3 and the movement speed decreases, and, as a result, the electric resistance increases.

Therefore, by measuring the variation of the electric resistance of the CuBr layer 3 through the two electrodes 4 and 5 electrically coupled with the CuBr layer 3, the concentration of aldehyde such as, for example, acetaldehyde or nonanal can be measured.

Incidentally, the effect of the carrier trap increases as the distance between the polarized structure formed by temporary coupling between amine and aldehyde and the surface of the p-type semiconductor layer 3 decreases. Therefore, it is preferable for an amino group contained in amine to be capable of coupling with atoms that configure the p-type semiconductor layer 3. Therefore, as described above, it is preferable to use a semiconductor material (here, CuBr) that is a compound of copper or silver containing, as a constituent element, a positive ion with which an amino group can form intensive coordinate bond.

Further, although basically any amine reacts with aldehyde, aldehyde immediately changes into imine by a reaction with primary amine and forms a reversible adduct by reaction with secondary amine. The substances generated from primary amine and secondary amine have a low polarized moment and a long life in comparison with the polarized structure obtained from tertiary amine 2 and aldehyde. Therefore, the tertiary amine 2 is particularly suitable in the variation of the resistance by carrier trap in the proximity of the surface of the p-type semiconductor layer 3 and the recovery speed after the contact with the detection target gas ends.

Further, since the tertiary amine 2 has a low nucleophilic attacking performance to ketone (ketones) having a chemical property proximate to that of aldehyde, the difference of the responsibility of the device can be increased between aldehyde and ketone. Further, while amine has the ability of forming an ion pair with alcohol by extracting a proton from a hydroxyl group of alcohol, different from the nucleophilic attack described above, such a variation as just described is difficult to achieve where there is no solvent in the surroundings. Therefore, the response as a gas sensor to alcohol becomes weak. Further, from the tertiary amine 2, a clear response to ammonia is not found. Accordingly, by using the tertiary amine 2, the present gas sensor has such a high gas type selectivity that the sensitivity to a chemical substance other than aldehyde, namely, to organic gas (gaseous organic compound) such as, for example, ammonia, ketone (for example, acetone), alcohol (for example, ethanol) or the like is low. In short, by using the tertiary amine 2, a gas sensor having a performance for intensively responding especially to aldehyde from among gaseous organic compounds can be implemented.

Further, since aldehyde that is considered promising, for example, as a marker of lung cancer forms a structure that hydrogen atoms and an alkyl group bonds to carbon atoms of a carbonyl group, in order to make it possible to obtain an intensive response to aldehyde, it is preferable to use such tertiary amine 2 as that in which all of atomic groups bonding to nitrogen atoms of an amino group are alkyl groups.

Accordingly, with the gas sensor according to the present embodiment, there is an advantage that a gas sensor can be implemented which can detect aldehyde with a high sensitivity and can distinguish the aldehyde from the other substances with a high selection ratio, for example, to such a degree that the gas sensor can be used for checking of lung cancer or the like.

EXAMPLE

The gas sensor is described below in more detail in connection with an example. However, the present embodiment is not limited to the example described below.

In the present example, first, two gold electrodes (a pair of gold electrodes; gold electrode films) 4 and 5 individually having a width of approximately 10 mm, a length of approximately 20 mm and a film thickness of approximately 30 nm were formed first across a gap of a distance of approximately 0.5 mm by vapor deposition using a mask on a silicon wafer with a thermal oxide film (silicon substrate; substrate) 6 having a length of approximately 50 mm, a width of approximately 10 mm and having a thermal oxide film (SiO$_2$ film; insulating film) 7 of a thickness of approximately 1 μm on the surface thereof (refer to FIG. 1).

Then, a cuprous bromide (CuBr) layer having a thickness of approximately 120 nm was formed as the p-type semiconductor layer 3 on the intermediate product just described (refer to FIG. 1).

Here, a film of copper having a film thickness of approximately 15 nm was formed first by vapor deposition using a mask so as to have a planar form having a width of approximately 8 mm and a length of approximately 30 mm. Then, the product just described was soaked in cupric bromide aqueous solution having a concentration of approximately 100 mM for 18 seconds. A CuBr layer 3 having a thickness of approximately 120 nm was formed by varying the copper film by the process just described (refer to FIG. 1).

Then, the surface of the CuBr layer 3 was covered with N, N-dimethyl-hexadecylamine that is the tertiary amine 2 (refer to FIG. 1).

Here, the surface of the CuBr layer 3 was covered with the N, N-dimethyl-hexadecylamine that is the tertiary amine 2 by a method that the product described above was soaked in hexane solution in which the concentration of the N, N-dimethyl-hexadecylamine was approximately 100 ppm for approximately 3 minutes at a room temperature and then the product just described was immediately left for approximately 3 minutes in a vertically standing state in a hexane saturation atmosphere, and surplus amine was washed away, whereafter the product was taken out into and left in the air so as to be dried.

The gas sensor device 1 of the present example was produced in such a manner as described above (refer to FIG. 1).

Then, a response of the gas sensor device 1 to various gas types was evaluated by providing the gas sensor device 1 produced in such a manner as described above in an nitrogen gas flow path whose flow rate is 4 L per one minute and changing over the gas source between pure nitrogen and nitrogen having an equal flow rate and containing detection target gas of a predetermined concentration to measure the resistance variation of the gas sensor device 1.

First, a response to ammonia having a concentration of approximately 300 ppb, another response to acetaldehyde having a concentration of approximately 300 ppb and a further response to nonanal having a concentration of approximately 200 ppb were evaluated.

Figure 5:
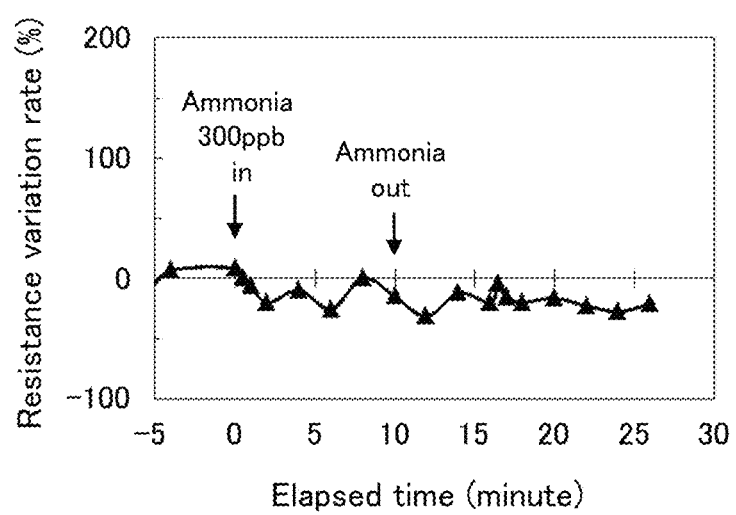
FIG. 5 is a view depicting a time variation of the variation rate of electric resistance where a gas sensor device of an example is exposed to a nitrogen stream containing ammonia having a concentration of approximately 300 ppb.
Figure 6:
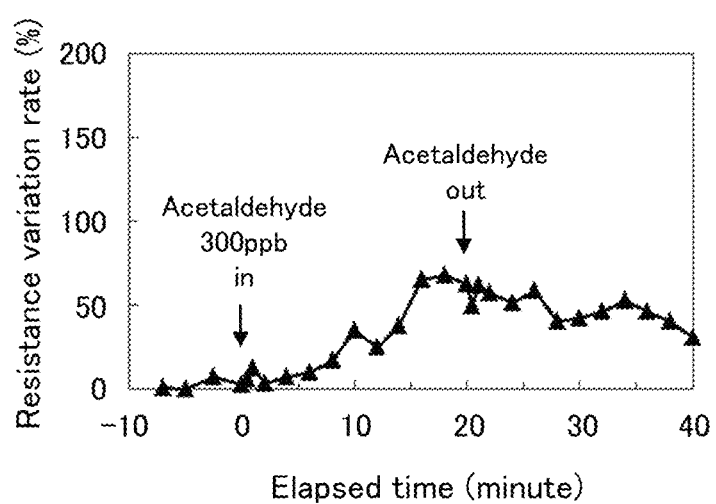
FIG. 6 is a view depicting a time variation of the variation rate of electric resistance where the gas sensor device of the example is exposed to a nitrogen stream containing acetaldehyde having a concentration of approximately 300 ppb.
Figure 7:
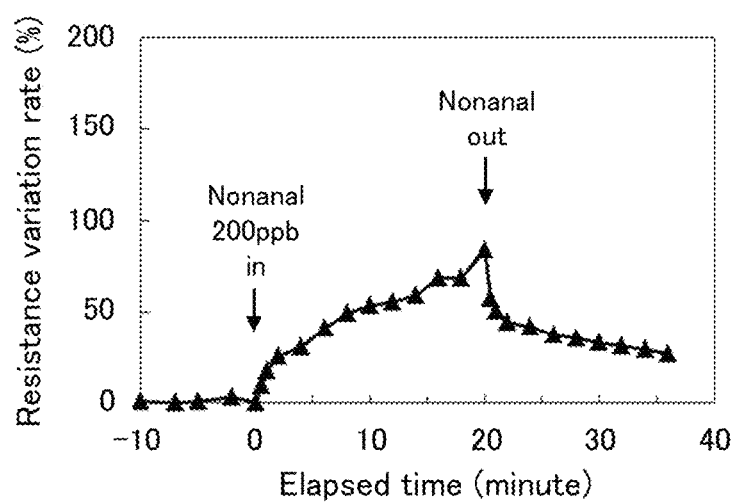
FIG. 7 is a view depicting a time variation of the variation rate of electric resistance where the gas sensor device of the example is exposed to a nitrogen stream containing nonanal having a concentration of approximately 200 ppb.

Here, FIGS. 5, 6 and 7 depict a response to ammonia having a concentration of approximately 300 ppb, another response to acetaldehyde having a concentration of approximately 300 ppb and a further response to nonanal having a concentration of approximately 200 ppb in the form of time variation of the resistance variation rate, respectively.

As depicted in FIG. 5, a clear response to ammonia having a concentration of approximately 300 ppb was not found. On the other hand, as depicted in FIG. 6, to acetaldehyde having a concentration of approximately 300 ppb, a resistance variation of approximately 60% was found for approximately 20 minutes. Further, as depicted in FIG. 7, to nonanal having a concentration of approximately 200 ppb, a resistance variation of approximately 80% was found for approximately 20 minutes.

Then, in addition to the three types of gases, also a response to acetone and another response to ethanol were further evaluated, and the responses (response intensities) to the gas types used for the evaluation were standardized with the concentrations of the gas types using the response (response intensity) to nonanal as a reference to calculate the ratio (selection ratio) to the response (response intensity) to nonanal. As a result of the calculation, such a result as depicted in FIG. 8 was obtained.

As depicted in FIG. 8, the gas sensor device of the present example exhibits an intensive response to aldehyde (nonanal and acetaldehyde) in comparison with the responses to ammonia, acetone and ethanol, and exhibits a selectively excellent response to aldehyde (nonanal and acetaldehyde).

Further, the gas sensor device of the example exhibits a response intensity of approximately 2 times that of nonanal whose carbon number is 9 with respect to acetaldehyde whose carbon number is 2.

This indicates that, by covering the surface of the CuBr layer with N, N-dimethyl-hexadecylamine that is tertiary amine that contains totaling 18 carbon atoms and in which 16 ones of the carbon atoms form a straight chain, the affinity to nonanal that is aldehyde containing an alkyl group having a great number of carbons is enhanced on the contacting face with gas and the gas sensor device contributes to implementation of such desirable selectivity as described above.

Comparative Example

In the present comparative example, a gas sensor device was produced in such manner as described below without covering the surface of a CuBr layer as a p-type semiconductor layer with N, N-dimethyl-hexadecylamine that is tertiary amine.

In particular, in the present comparative example, similarly as in the example described above, two gold electrodes (a pair of gold electrodes; gold electrode films) individually having a width of approximately 10 mm, a length of approximately 20 mm and a thickness of approximately 30 nm were formed across a gap having a distance of approximately 0.5 mm by vapor deposition using a mask on a silicon wafer with a thermal oxide film (silicon substrate) having a length of approximately 50 mm and a width of approximately 10 mm and having a thermal oxide film ($SiO_2$ film) of a thickness of approximately 1 μm on the surface thereof.

Then, a cuprous bromide (CuBr) layer having a thickness of approximately 250 nm was formed as a p-type semiconductor layer on the product.

Here, a film of copper having a film thickness of approximately 30 nm was formed by vapor deposition using a mask so as to have a planar form having a width of approximately 8 mm and a length of approximately 30 mm. Then, the product was soaked in cupric bromide aqueous solution having a concentration of approximately 100 mM for approximately 20 seconds. A CuBr layer having a thickness of approximately 250 nm was formed by varying the copper film by the process just described.

The gas sensor device of the present comparative example was produced in such a manner as described above.

Then, a response of the gas sensor device produced in such a manner as described above to each gas type was evaluated by providing the gas sensor device in a nitrogen gas flow path whose flow rate was 4 L per 1 minute and changing over the gas source between pure nitrogen and nitrogen having an equal flow rate and containing detection target gas of a predetermined concentration to measure the resistance variation of the gas sensor device.

First, a response to ammonia having a concentration of approximately 300 ppb and another response to acetaldehyde having a concentration of approximately 300 ppb were evaluated.

Figure 9:
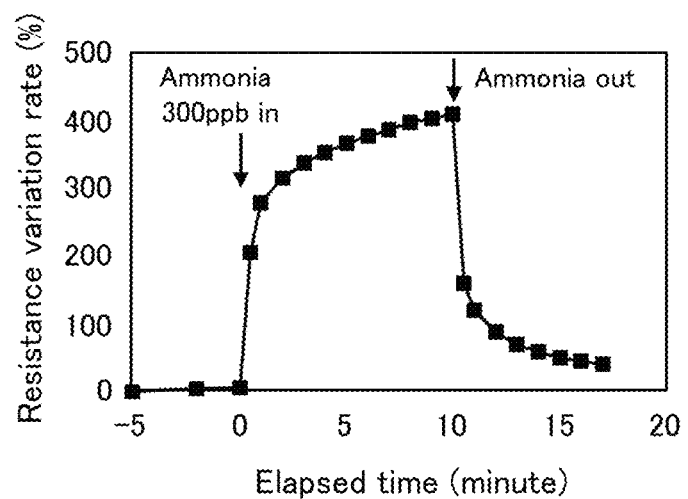
FIG. 9 is a view depicting a time variation of the variation rate of electric resistance where a gas sensor device of a comparative example is exposed to a nitrogen stream containing ammonia having a concentration of approximately 300 ppb.
Figure 10:
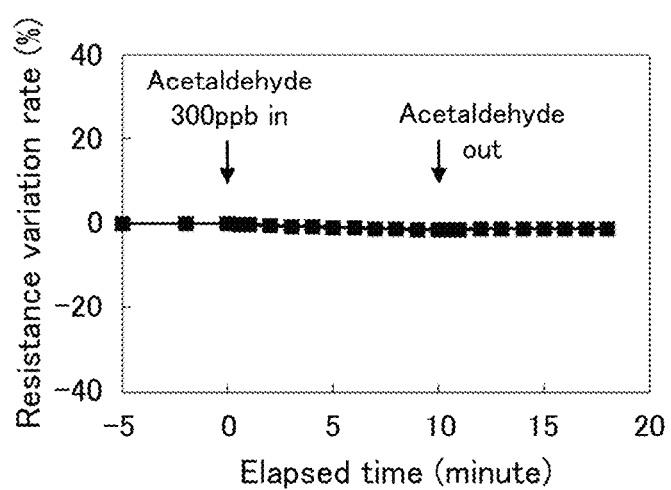
FIG. 10 is a view depicting a time variation of the variation rate of electric resistance where the gas sensor device of the example is exposed to a nitrogen stream containing acetaldehyde having a concentration of approximately 300 ppb.

Here, FIGS. 9 and 10 depict a response to ammonia having a concentration of approximately 300 ppb and another response to acetaldehyde having a concentration of approximately 300 ppb each in the form of a time variation of the resistance variation rate, respectively.

As depicted in FIG. 9, to ammonia having a concentration of approximately 300 ppb, a resistance variation of approximately 400% was exhibited for approximately 10 minutes. On the other hand, as depicted in FIG. 10, a clear response was not exhibited to acetaldehyde having a concentration of approximately 300 ppb.

Then, also a response to ethanol was evaluated in addition to two types of gas, and the responses (response intensities) to the gas types used for the evaluation were standardized with the concentrations of the gas types using the response (response intensity) to ammonia as a reference to calculate ratios (selection ratios) to the response (response intensity) to ammonia. As a result of the calculation, such a result as depicted in FIG. 11 was obtained.

As depicted in FIG. 11, the gas sensor device of the present comparative example exhibits an intensive response to ammonia and a selectively excellent response to ammonia in comparison with the response to aldehyde (acetaldehyde) or ethanol. In other words, the gas sensor device of the present comparative example did not effectively operate as a gas sensor device that selectively exhibits a response to aldehyde.

Incidentally, the gas sensor of the embodiment described above may include not only the gas sensor device 1 but also, for example, a circuit as a detection unit, a processor, a memory, a communication circuit and so forth.

Further, the gas sensor may include a display screen such that a value (for example, a resistance value) detected by the gas sensor device 1 and the circuit as the detection unit is converted into a value indicating the concentration of aldehyde and the resulting value is displayed as a parameter indicating the concentration of aldehyde on the display screen.

Figure 12:
FIGS. 12 and 13 are schematic views depicting examples of a configuration of an information processing system according to the present embodiment.

Further, for example, as depicted in FIG. 12, a gas sensor 10 including such a gas sensor device 1 as described above may be coupled with a computer 11 such as, for example, a personal computer such that data measured using the gas sensor 10 is transmitted to the computer 11. In this case, the data obtained by the gas sensor 10 may be processed by the computer 11, and then a parameter indicating the concentration of aldehyde, presence or absence of a disease or the like may be displayed on the screen of the computer 11.

In this case, an information processing system for performing such a data process (information process) as just described may include the gas sensor 10 including the gas sensor device 1 of the embodiment described above and the computer 11 coupled with the gas sensor 10 for processing the data obtained by the gas sensor 10. It is to be noted that such an information processing system as just described is called gas evaluation system.

Also it is possible to collect and accumulate data (information) measured using a gas sensor including such a gas sensor device 1 as described above through a network to construct a database or analyze the collected and feed back a result of the analysis.

By the configuration described above, the information processing system is effectively utilized for improvement of the screening accuracy of a disease, checking of presence or absence of a correlation with some other disease or the like, and it is possible to feedback a result of the measurement without requiring much effort. For example, by analyzing presence or absence of cancer in a measurement target of the breath or a correlation with some other disease, enhancement of the screening accuracy and development to screening of some other disease can be implemented.

Figure 13:
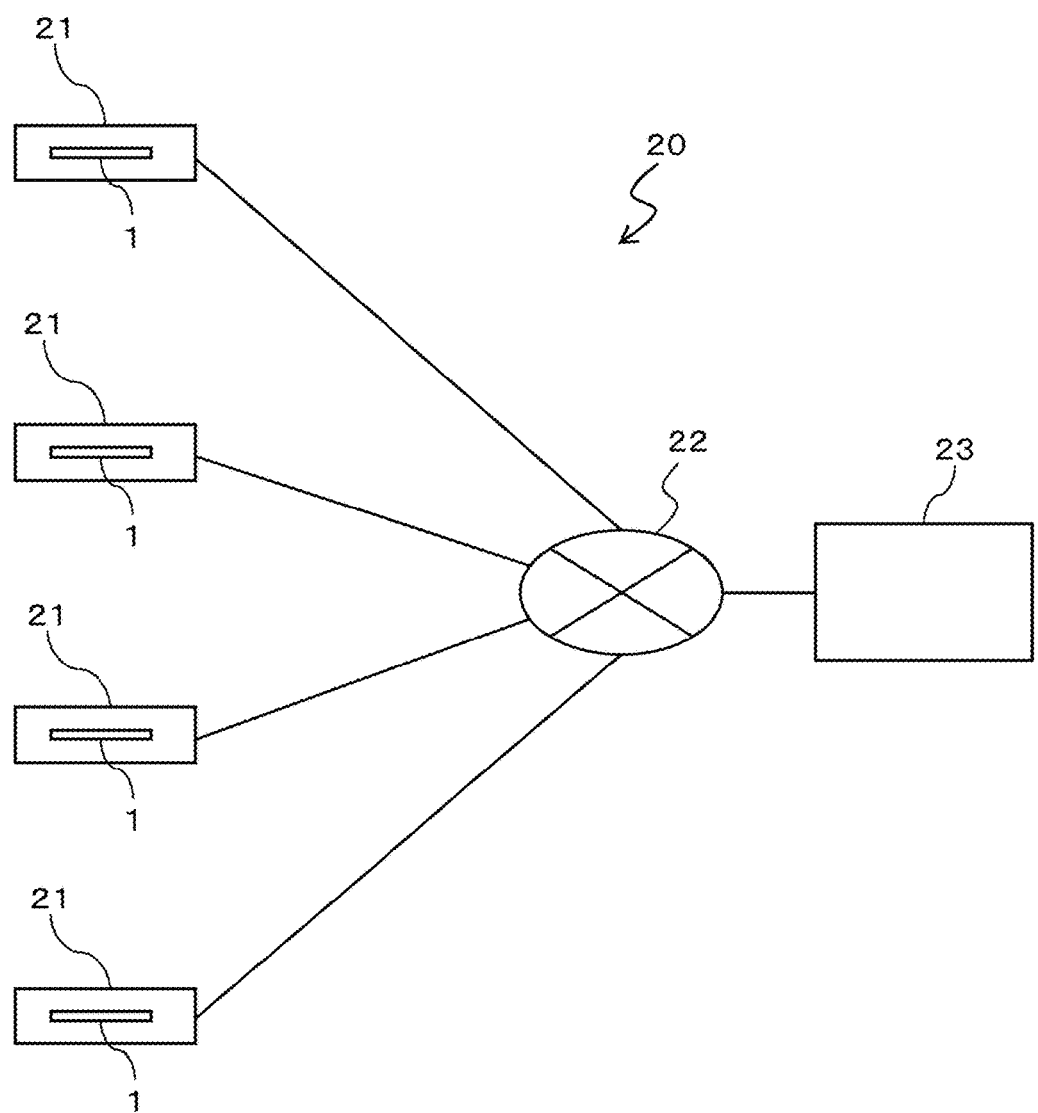

In this case, as depicted in FIG. 13, an information processing system 20 that performs such a data process (information process) as described above may include a gas sensor 21 including the gas sensor device 1 of the embodiment described above and a server (computer) 23 coupled with the gas sensor 21 through a network 22 for processing data obtained by the gas sensor 21. It is to be noted that such an information processing system as just described is also called gas evaluation system.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A gas sensor, comprising:
a p-type semiconductor layer whose first surface as a top surface or as at least a portion of a top surface is covered with tertiary amine such that aldehyde is detected selectively; and
two electrodes electrically coupled with each other through the p-type semiconductor layer, the two electrodes being in contact with a second surface as opposing bottom surfaces or as portions of opposite sides of the portion of the top surface other than the first surface of the p-type semiconductor layer,
wherein the surface of the tertiary amine is exposed such that the detection target gas contacts at least with the surface of the tertiary amine over a region between the two electrodes, and
the p-type semiconductor layer contains any one material selected from the group consisting of cuprous bromide, cuprous oxide, cuprous sulfide, silver oxide, silver bromide and silver sulfide.

2. The gas sensor according to claim 1, wherein, in the tertiary amine, all of atomic groups bonding to nitrogen atoms of an amino group are an alkyl group.

3. The gas sensor according to claim 1, wherein the two electrodes are provided in a spaced relationship from each other on the second surface positioned at the opposite side to the first surface side of the p-type semiconductor layer.

4. The gas sensor according to claim 1, further comprising a detection unit coupled with the two electrodes and configured to detect variation of an electric characteristic of the p-type semiconductor layer.

5. An information processing system, comprising:
a gas sensor including a p-type semiconductor layer whose first surface as a top surface or as at least a portion of a top surface is covered with tertiary amine such that aldehyde is detected selectively and two electrodes electrically coupled with each other through the p-type semiconductor layer, the two electrodes being in contact with a second surface as opposing bottom surfaces or as portions of opposite sides of the portion of the top surface other than the first surface of the p-type semiconductor layer, wherein the surface of the tertiary amine is exposed such that the detection target gas contacts at least with the surface of the tertiary amine over a region between the two electrodes, and the p-type semiconductor layer contains any one material selected from the group consisting of cuprous bromide, cuprous oxide, cuprous sulfide, silver oxide, silver bromide and silver sulfide; and
a computer configured to process data obtained by the gas sensor.

* * * * *